United States Patent [19]

Marotta et al.

[11] Patent Number: 4,684,649
[45] Date of Patent: Aug. 4, 1987

[54] QUINOXALINE DERIVATIVES USEFUL FOR TREATMENT AND PROPHYLAXIS OF SWINE DYSENTERY AND AS ANIMAL GROWTH PROMOTANTS

[76] Inventors: Enrico Marotta; Lucia Castronuovo, both of Via Andrea Verga 8, 20144 Milan, Italy

[21] Appl. No.: 825,643

[22] Filed: Feb. 3, 1986

[30] Foreign Application Priority Data

Mar. 1, 1985 [GB] United Kingdom ............... 8505286

[51] Int. Cl.$^4$ ................. C07D 241/52; A61K 31/495
[52] U.S. Cl. ...................................... 514/249; 544/353
[58] Field of Search ................. 544/353, 355; 514/249

[56] References Cited

U.S. PATENT DOCUMENTS

| | | | |
|---|---|---|---|
| 3,344,022 | 9/1967 | Johnston | 544/353 |
| 3,474,097 | 10/1969 | Johnston | 544/353 |
| 3,816,630 | 6/1974 | Bowie et al. | 514/249 |
| 4,086,345 | 4/1978 | Garzia et al. | 514/249 |
| 4,634,702 | 1/1987 | Gatti | 544/353 |

FOREIGN PATENT DOCUMENTS 1041011  9/1966  United Kingdom ............... 544/353

*Primary Examiner*—Mark L. Berch
*Assistant Examiner*—Emily Bernhardt

*Attorney, Agent, or Firm*—Oblon, Fisher, Spivak, McClelland & Maier

[57] ABSTRACT

The present invention concerns quinoxaline derivatives of the structural formula I:

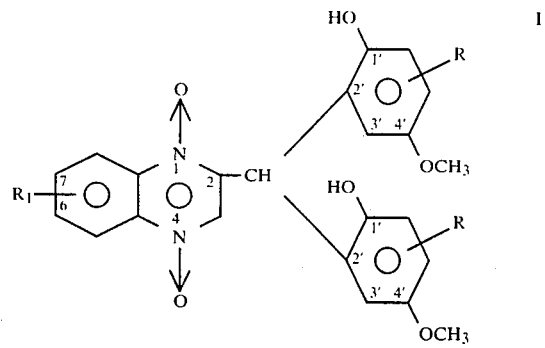

wherein the two substituents R on the phenyl rings are equal or different and represents $C_1$–$C_5$ lower alkyl, and $R_1$ is a 6- or 7-position substituent selected from the group consisting of hydrogen, halogen, lower alkyl, lower alkoxy and lower alkanoyl.

Such compounds have been found useful in preventing swine dysentery as well as being used as animal growth promotants.

8 Claims, No Drawings

QUINOXALINE DERIVATIVES USEFUL FOR TREATMENT AND PROPHYLAXIS OF SWINE DYSENTERY AND AS ANIMAL GROWTH PROMOTANTS

This invention relates to quinoxaline derivatives which are useful antiinfective agents for the control of various pathogenic microorganisms and as animal growth promotants. Among the animal infectious diseases caused by pathogenic microorganisms which can be controlled by the compounds of the present invention there are the following ones: chronic respiratory disease in poultry, infectious sinusities in turkeys, and, especially swine dysentery. Swine dysentery is a severe mucohemmorrhagic diarrheal disease that primarily affects pigs during the growing-finishing period. Swine dysentery occurs in most swinerearing areas of the world. The primary etiologic agent of swine dysentery is an anaerobic spirochete called *Treponema hyodysenteriae*.

Various analogs of the compounds of the present invention are known in the prior art to be useful for such purposes. Typical examples of these prior art analogs are disclosed in U.S. Pat. Nos. 3,344,022; 3,371,090; 3,558,624; 4,086,345; 4,128,642.

Whereas these prior art analogs showed useful activity for the stated purposes, it has been found that they display certain toxic side effects. For example 2-formyl-quinoxaline-1,4-dioxide carbomethoxyhydrazone disclosed and claimed in the above mentioned U.S. Pat. No. 3,371,090 and with the generic name carbadox has proved to exhibit a substantial mutagenic effect. This effect of chemotherapeutic active substances is conveniently determined according to the "Ames test" (B.N. Ames et al. Mutation Research 31, page 347, 1975).

Unexpectedly, it has been found that the compounds of the present invention display a marked reduction in these untoward effects, and they may, therefore, be used with a higher degree of safety or in larger amounts for a quicker control of various pathogenic microorganisms and for the acceleration of animal growth rate and for improved feed efficiency. Object of the present invention is therefore a new series of 2-[bis(1'-hydroxy-4'-methoxy-phenyl 2')-methyl]-quinoxaline-1,4-dioxide derivatives of the structural formula I

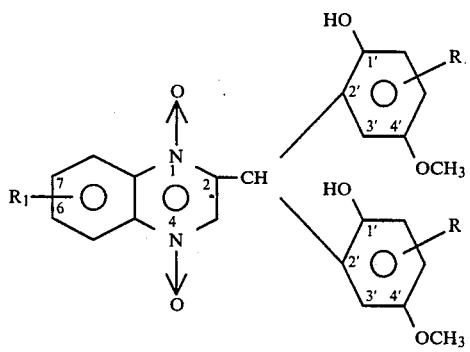

wherein the two substituents R on the phenyl rings are equal or different and represents $C_1$–$C_5$ lower alkyl, preferably t-butyl- and $R_1$ is a 6- or 7-position substituent selected from the group consisting of hydrogen, halogen, lower alkyl, lower alkoxy and lower alkanoyl.

By the terms lower alkyl, lower alkoxy, and lower alkanoyl are meant those groups which contain from 1 to 4 carbon atoms, i.e. those which are conveniently prepared from readily available starting materials.

The compound of this invention of formula I may be prepared by reacting 2 moles of a suitable phenoxy magnesium halide derivative of structure II with 1 mole of a 2-formyl-quinoxaline-1,4-dioxide of formula III

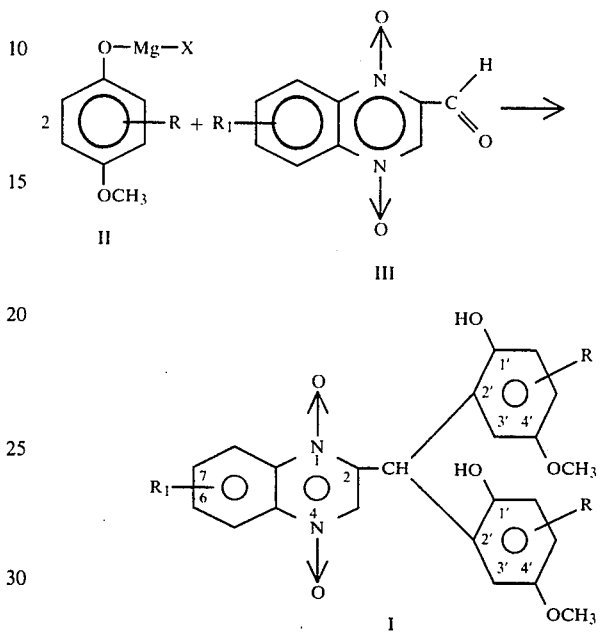

wherein R and $R_1$ have the above meaning, and X is Cl or Br.

The reaction is carried out in an anhydrous apolar organic solvent such benzene, toluene or xylene under nitrogen atmosphere.

The reaction starts at room temperature, but it is preferred to complete it at warm temperature, preferably at the boiling temperature of the solvent employed. The time reaction may vary from a few minutes to several hours according to the reaction employed. The molar ratio between the phenoxy magnesium halide derivative II and the 2-formyl-quinoxaline-1,4-dioxide derivative III is 2:1, but it is preferred to use a slight excess of II.

When the reaction is over the solution is cooled to room temperature and it is neutralized with a dilute aqueous inorganic acid such hydrochloric or sulfuric acid.

The organic layer is separated, washed and evaporated "in vacuo" to dryness. The residue is then purified by crystallization.

The phenoxy magnesium halide II, generally chloride or bromide must be prepared separately according to known methods usually employed in the Grignard reactions. The desired phenol derivative of structure:

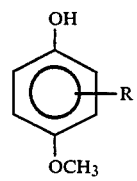

wherein R has the above meaning, dissolved in an anhydrous linear or cyclic ether such as ethyl ether, tetrahydrofuran or dioxane is added at room temperature to an equimolecular solution of methyl- or ethyl-magnesium chloride or bromide in ethyl ether.

This solution of methyl- or ethyl-magnesium chloride or bromide was previously prepared and kept under nitrogen. After formation of the desired phenoxy magnesium halide II, most part of the ether solvent is removed by distillation under reduced pressure of nitrogen.

Always under nitrogen atmosphere anhydrous benzene or toluene is cautiously added.

The 2-formyl-quinoxaline-1,4-dioxide derivative III also dissolved in anhydrous benzene or toluene is now added dropwise with stirring and allowed to react as indicated above.

Preferred compounds of the present invention are those in which $R_1$ is hydrogen, and those in which both substituents R on the phenyl ring are t-butyl.

The preferred compound is that in which $R_1$ is hydrogen and the t-butyl substituent is located at the ortho-position with respect to the methoxy-group in the phenyl ring.

The compounds of the present invention are generally white-yellow crystalline powder, almost tasteless or slightly bitter.

They are soluble in dimethylformamide and tetrahydrofuran, slightly soluble in aromatic hydrocarbon, acetone and lower alcohols, and they are sparingly or almost insoluble in water.

When administered at pharmaceutically effective dosage levels, these compounds are antibacterial agents useful in animal health care. They have been found to cure some infectious diseases in animals such as poultry goats, sheep, horses, cattle and swine. The novel compounds of the present invention exhibit excellent activity against swine salmonellosis and in particular against swine dysentery caused by *Treponema hyodysenteriae*.

As briefly mentioned above the novel compounds of the present invention have shown to be completely free from any mutagenic effect according to the "Ames test" (B.N. Ames et al - Mutation Research 31, page 347, 1975). In addition the compounds of the present invention are effective animal growth promotants particularly for swine and poultry. The animals thus attain market size sooner and on less feed.

The in vitro broad spectrum antibacterial activity of these compounds is demonstrated by determining minimum inhibitory concentration (MIC).

MIC's against *Treponema hyodysenteriae* were determined by spreading appropriate dilutions of the microorganism on a growth medium containing about 5% bovine blood and about 3% tryptose agar.

Among the compounds of structure I subjected to in vitro screening were the following in which R and $R_1$ have the above meaning.

The numbers in the right column with respect to R and $R_1$ indicate the position of the substituent in the phenyl and quinoxaline rings, respectively.

Acute systemic infections in mice have been used to evaluate the in vivo therapeutic activity of compound of Example 1.

These infections are produced by the intraperitoneal injection of standard cultures suspended in hog gastrin mucin. Half an hour after inoculation the treatment was set up. Efficacy may be measured in $ED_{50}$ i.e. the dose of the compound in mg/Kg body weight required to protect 50% of the treated animals against otherwise lethal infections. The compounds were administered both orally and subcutaneously. The results are given below. The compound of the present invention may be administered orally or parenterally.

When administered orally for prophylactic purposes, the compounds are usually blended into a nutritionally balanced feed at a level of one to 300 grams per ton. For therapeutic purposes higher dosage levels may be employed. Typical nutritionally balanced feed for hogs are shown in the table below.

| | Kg. per ton of feed |
|---|---|
| Ground Corn | 956.000 |
| Dicalcium phosphate | 12.900 |
| Calcium carbonate | 14.900 |
| Mixture of vitamins A,D niacin, calcium pantothenate | 3.240 |
| Choline | 3.240 |
| Mineral salts | 3.240 |
| Inorganic iodides | 6.480 |

Toxicity

The toxicity of the compounds of the present invention is very low: in the rat the $LD_{50}$ is 600 mg/kg b.w. by intraperitoneal route and more than 5000 mg/kg b.w. by oral route.

The following Examples are solely for the purpose of illustration only and are not to be construed as limitations of this invention.

EXAMPLE 1

2-[bis(1'-hydroxy-3'-t-butyl-4'-methoxy-phenyl-2')-methyl]-quinoxaline-1,4-dioxide A solution of 360 g of 3-t-butyl-4-methoxyphenol (2 mol) in 1000 ml of anhydrous peroxide-free tetrahydrofuran was purged of atmospheric oxygen by bubbling nitrogen therethrough for about three minutes. To this solution cooled to 0° C. a solution of 2 mol of methyl-magnesium-bromide in 1200 ml of anhydrous tetrahydrofuran previously prepared under nitrogen was added over 20 minutes with stirring. Most of the tetrahydrofuran was removed by distillation under nitrogen. Then 4000 ml of anhydrous benzene were added. A solution of 190 g of 2-formyl-quinoxaline-1,4-dioxide (1 mol) in 1000 ml of anhydrous benzene was added to the previous solution under nitrogen with stirring. Stirring was continued at room temperature overnight and then the reaction mixture was heated with stirring under reflux for 1 hour. After cooling to room temperature the mixture was poured into a suitable separatory funnel and neutralized with 10% aqueous hydrochloric acid

| Compound of Example | R | $R_1$ | mp.(C) | MIC (µg/ml) | Position of R/$R_1$ Substituent on Ring |
|---|---|---|---|---|---|
| 1 | t-butyl | H | 150° C. dec. | 0,1 | 3'/— |
| 2 | i-propyl | H | 175 | 0,9 | 3'/— | and thoroughly shaken. The organic layer was separated, washed and evaporated "in vacuo" to dryness. The residue was recrystallized from acetone.

280 g of purified compound were obtained. PMR and IR spectrum confirmed the expected structure. Empirical formula: $C_{31}H_{36}N_2O_6$.

|  | Calculated | Found |
|---|---|---|
| % C | 69.92 | 69.95 |
| % H | 6.76 | 6.80 |
| % O | 18.04 | 17.98 |
| % N | 5.26 | 5.30 |

The compound is soluble in dimethylformamide, tetrahydrofuran and dioxane. It is slightly soluble in benzene, acetone, methanol. It is very scarcely soluble in water. Heated above 150° C. it decomposes without melting.

Comparable result was achieved when methyl-magnesium-chloride was used instead of methyl magnesium bromide.

EXAMPLE 2

2-[bis(1'-hydroxy-3'-i-propyl-4'-methoxy-phenyl-2')-methyl]-quinoxaline-1,4-dioxide By operating according to the method described in Example 1 but by replacing 3-t-butyl-4-methoxy-phenol with 3-i-propyl-4-methoxy-phenol, the title compound was obtained (m.p. 175° C. with decomposition).

EXAMPLE 3

2-[bis(1'-hydroxy-3'-ethyl-4'-methoxy-phenyl-2')-methyl]-quinoxaline-1,4-dioxide By operating according to the method described in Example 1 but by replacing 3-t-butyl-4-methoxy-phenol with 3-ethyl-4-methoxy-phenol, the title compound was obtained (m.p. 189° C. with decomposition).

EXAMPLE 4

2-[bis(1'-hydroxy-3'-t-butyl-4'methoxy-phenyl-2')-methyl]-6-chloro-quinoxaline-1,4-dioxide By operating according to the method described in Example 1, but by replacing 2-formyl-quinoxaline-1,4-dioxide with 2-formyl-6-chloro-quinoxaline-1,4-dioxide the title compound was obtained.

EXAMPLE 5

2-[bis(1'-hydroxy-3'-t-butyl-4'-methoxy-phenyl-2')-methyl]-6-methyl-quinoxaline-1,4-dioxide By operating according to the method described in Example 1, but by replacing 2-formyl-quinoxaline-1,4-dioxide with 2-formyl-6-methyl-quinoxaline-1,4-dioxide the title compound was obtained.

EXAMPLE 6

Compound of Example 1 was mixed with the swine balanced feed described on page 8 at the ratio of 200 grams/ton. A group of 30 pigs was fed with this medicated diet. An equivalent group of pigs was used as control. The two groups were stabled in pigsties where infections of Treponema hyodysenterae have been observed. No one of the animals under treatment was getting ill, while the 50% of the untreated animals in the control group was clearly showing typical symptoms of swine dysentery. The infected animals recovered completely after 2 weeks of treatment with the above mentioned medicated feed.

EXAMPLE 7

The efficacy of compound of Example 1 in promoting growth and improving the feed efficiency is illustrated below. 20 healthy pigs of same age and of average same weight were divided into two groups. One group of 10 pigs served as control and was fed a basal non-supplemented diet, the other group of 10 pigs received the same basal diet, but supplemented with 200 grams/ton of compound of Example 1.

After 28 days treatment, the pigs on the supplemented diet are, on the average, 4,6% heavier than the pigs which received the control ration and demonstrated a 5,5% increase in feed efficiency over the controls.

EXAMPLE 8

Mutation Test determined according to the "Ames test"

(B.N. Ames et al. Mutation Research 31, page 347, 1975).

The compound 2-[bis-(1'-hydroxy-3'-t-butyl-4'-methoxy-phenyl-2')-methyl-quinoxaline-1,4-dioxide prepared according to Example 1 was submitted to the Ames test showing the results summarized in the following two tables:

TABLE 1

| | (in the absence of microsomial extract) | | | |
|---|---|---|---|---|
| Quantity | Number of mutating colonies/plate with strains of Salmonella Typhimurium | | | |
| (in mcg) | TA 1538 | TA 1535 | TA 98 | TA 100 |
| of the tested compound | | | | |
| 0 | 31 | 28 | 24 | 164 |
| 10 | 11 | 15 | 25 | 168 |
| 30 | 16 | 12 | 24 | 165 |
| 100 | 15 | 9 | 27 | 151 |
| 300 | 10 | 13 | 24 | 162 |
| 600 | 17 | 25 | 27 | 177 |
| 1000 | 17 | 16 | 27 | 142 |
| of sodium azide | | | | |
| 10 | — | 1006 | — | — |

TABLE 2

| | (in the presence of microsomial extract) | | | |
|---|---|---|---|---|
| Quantity | Number of mutating colonies/plate with strains of Salmonella Typhimurium | | | |
| (in mcg) | TA 1538 | TA 1535 | TA 98 | TA 100 |
| of the tested compound | | | | |
| 0 | 28 | 28 | 29 | 163 |
| 10 | 16 | 23 | 30 | 158 |
| 30 | 14 | 26 | 27 | 143 |
| 100 | 15 | 22 | 24 | 135 |
| 300 | 8 | 16 | 20 | 174 |
| 600 | 18 | 22 | 24 | 175 |
| 1000 | 14 | 20 | 28 | 125 |
| of sodium azide | | | | |
| 10 | 2258 | — | 1803 | — |

What is claimed is:

1. A compound of the structure I:

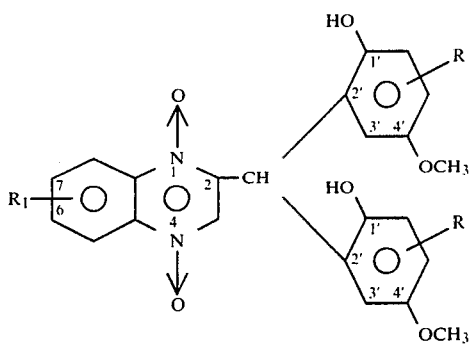

wherein the two substituents R on the phenyl rings are equal or different and represents $C_1-C_5$ lower alkyl, and $R_1$ is a 6- or 7-position substituent selected from the group consisting of hydrogen, halogen, $C_1-C_4$ lower alkyl, $C_1-C_4$ lower alkoxy and $C_1-C_4$ lower alkanoyl.

2. A compound of claim 1 which is 2-[bis(1'-hydroxy-3'-t-butyl-4'-methoxy-phenyl-2')-methyl]-quinoxaline-1,4-dioxide.

3. A compound of claim 1 which is 2-[bis(1'-hydroxy-3'-i-propyl-4'-methoxy-phenyl-2')-methyl]-quinoxaline-1,4-dioxide.

4. A compound of claim 1 which is 2-[bis(1'-hydroxy-3'-ethyl-4'-methoxy-phenyl-2')-methyl]-quinoxaline-1,4-dioxide.

5. A method of controlling swine dysentery which comprises administering to said animals a pharmaceutically effective amount of a compound of claim 1.

6. A method of promoting growth and improving feed efficiency of animals which comprises administering to said animals a pharmaceutically effective amount of a compound of claim 1.

7. An animal feed composition which comprises a nutritionally balanced animal feed containing a compound of claim 1 in the ratio from 1 to 300 g per ton of feed.

8. An animal feed composition according to claim 7 in which the compound is 2-[bis(1'-hydroxy-3'-t-butyl-4'-methoxy-phenyl-2')-methyl]-quinoxaline-1,4-dioxide.

* * * * *